(12) United States Patent
Baggott

(10) Patent No.: US 6,534,097 B1
(45) Date of Patent: Mar. 18, 2003

(54) PEST REPELLENT

(76) Inventor: Betty Baggott, 1012Towanda Rd., Virginia Beach, VA (US) 23464

( * ) Notice: Subject to any disclaimer, the term of this patent is extended or adjusted under 35 U.S.C. 154(b) by 0 days.

(21) Appl. No.: 10/192,950

(22) Filed: Jul. 11, 2002

(51) Int. Cl.$^7$ .................. A01N 59/02; A01N 59/06; A01N 37/44; A01N 63/00
(52) U.S. Cl. .................. 424/708; 424/687; 424/581; 424/93.1; 424/93.7; 424/DIG. 10; 514/562; 514/919
(58) Field of Search ................ 424/708, 687, 424/581, 93.1, 93.7, DIG. 10; 514/562, 919

(56) References Cited

U.S. PATENT DOCUMENTS

| | | | | |
|---|---|---|---|---|
| 1,044,452 A | * | 11/1912 | Halland | ............... 424/705 |
| 1,560,558 A | * | 11/1925 | Fulton et al. | ............... 424/715 |
| 4,726,144 A | * | 2/1988 | Young et al. | ............... 47/58 |

OTHER PUBLICATIONS

Frear, Donald E. Chemistry of Insecticides, Fungicides and Herbicides. D. Van Nostrand Co., Toronto, 1948, pp. 245–246.*

* cited by examiner

*Primary Examiner*—John Pak
(74) *Attorney, Agent, or Firm*—Bradley D. Goldizen

(57) ABSTRACT

A pest deterrent compound includes water, calcium carbonate and hydrogen sulfide. The compound is successful in deterring white flies and other destructive insects from attacking plants. The plant is protected by pouring a liquid solution onto the plant and the ground underneath and around the plant. The compound is absorbed into the plant's leaves and roots and acts as a deterrent against destructive insects. The pest deterrent compound is given in the following formula.

(1) H—O—H
(2) H—S—H

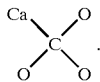
(3)

11 Claims, No Drawings

PEST REPELLENT

There are no related patent applications.
This invention was not federally funded.

BACKGROUND OF THE INVENTION

The present invention relates generally to pest repellant compounds. More particularly, the invention relates to a compound for repelling sucking insects such as white flies, mites and other types of destructive insects. The compound is especially effective in protecting poinsettia and gardenia plants.

White flies are small snow-white insects that resemble moths. When viewed with the naked eye, white flies typically resemble flying dandruff. They are destructive insects that feed by sucking plant juices, thus depleting the plants of vital nutrients. Leaves of plants that are infested with white flies may have spots or blotches of different colors or shades. If left alone, the leaves of an infested plant will yellow and the plant will eventually die.

A harmful secondary effect created by white flies is a honeydew type material that is excreted by these insects. This sticky material glazes the leaf surface, thereby permitting the development of black mold fungus. The black mold fungus interferes with photosynthesis and retards plant growth.

White flies have many species and attack a wide variety of plants. Examples of plants attacked by white flies include bedding plants, cotton, strawberries, vegetables, and poinsettias.

Traditional methods of treating infestations of white flies include applying potent pesticides to infected plants for extended periods of time. Applications of pesticides on infected plants enjoy limited success. Since white flies have two life stages, they are tolerant to most insecticides. In order to properly treat plants that are infested with white flies, the pesticides must be sprayed onto the under surfaces of the leaves of the infected plants.

Another method of controlling the populations of white flies is the use of predatory insects that consume white flies. This method is somewhat successful in greenhouse or closed environments. In open-air environments, the predatory insects may be consumed by birds and other predators that are higher on the food chain. Also, predatory insects may migrate from the plants to be protected when used in open-air environments.

Another technique for controlling white fly populations requires the use of a vacuum infiltration with soap solutions. This method causes the white flies to explode. In this method, an infected plant is placed in a soap solution. The plant is then put into a vacuum chamber and a vacuum is drawn. Since the white fly's body is comprised mostly of gas, the gas is drawn out when the vacuum is drawn. When the vacuum is released, the soap solution is drawn into the fly's body. The fly expands until it ruptures. While this method is effective in reducing the population of white flies, it is time intensive and requires special equipment.

While the aforementioned techniques have demonstrated limited success in treating infestations of white flies, these techniques are rarely a total solution for treating plants with infestations. Moreover, the techniques are not cost effective. The present invention intends to teach a superior method of treating plants that are infested with white flies.

BRIEF SUMMARY OF THE INVENTION

The present invention provides a pest repellant composition that is effective for controlling harmful pests, specifically white flies. It also teaches a cost-effective process for manufacturing the composition by using recycled by-products.

The present composition includes a mixture of water ($H_2O$), calcium carbonate ($CaCO_3$) and hydrogen sulfide ($H_2S$). The preferred mixture of the composition is 250 ml $H_2O$, 24.3 g $CaCO_3$ and 0.424 mg/l $H_2S$. To properly treat plants, the mixture should be present in an amount of ½ milligram per liter of water. The composition may also include food coloring or propylene ($C_3H_6$). The preferred food colors are FD&C #1 blue, #5 yellow or #6 yellow. Typically, the composition includes one drop of #1 blue and 0.5 drop of #5 or #6 yellow.

The present invention also contemplates a cost effective method of producing the above composition. The process includes adding eggshells with a portion of the albumen to hot or warm water and allowing this mixture to cure or ferment for several days. In the preferred embodiment, the mixture is allowed to cure for at least twelve days. The amount of time necessary to appropriately cure the mixture may vary according to different temperatures and various environmental conditions. Concentrated amounts of the present composition may be produced by adding additional quantities of albumen to the composition. The concentrated composition may be later added to water to produce large amounts of the composition.

It is an object of the invention to provide a cost effective way of dealing with infestations of white flies.

It is also an object of the invention to provide an environmentally safe method of treating plants to repel harmful insects such as white flies.

It is a further object of the invention to provide a pest repellant that is safe to human and animals.

It is another object of the invention to provide a repellant that provides nutritional value to the treated plant.

It is another object of the invention to provide a cost effective and easy method for producing the compound.

It is still another object of the invention to use recyclable waste by-products to produce the compound.

These objects and others will become apparent when the aforementioned discussion is taken in conjunction with the following disclosure.

DETAILED DESCRIPTION OF THE INVENTION

The following is the preferred embodiment or best mode for carrying out the invention. It should be noted that this invention is not limited by the discussion of the preferred embodiment.

There are many parts of an egg including the albumen or egg white. Typically, the albumen accounts for about sixty-seven percent of an egg's weight. The albumen contains more than half of the egg's total protein, minerals and vitamins. The albumen contains protein, niacin, riboflavin, chlorine, magnesium, potassium, sodium and sulfur.

The pest repellant is produced by fermenting eggshells with a portion of the albumen attached thereto. Fermentation is the chemical process that breaks down organic materials. The process is carried out by bacteria, molds and yeasts that are present in the air. It is believed that the fermentation process liberates sulfur from sulfates and sulfides present in the amino acids of the eggshells and albumen.

A chemical analysis of chicken eggs was undertaken and the following results were yielded. One-hundred grams of fresh chicken eggs contains approximately 70.83 g of water, 12.14 g of protein and 11.15 g of lipids. Minerals present in the eggs were as follows: 56 mg of C, 2.09 mg of Fe, 12 mg of Mg, 180 mg of P, 130 mg of K, 138 mg of Na and 1.44 mg of Zn. Vitamins included in the fresh eggs were as follows 0.087 mg of Thiamin, 0.301 mg of Riboflavin, 0.062 mg of Niacin, 0.120 mg of B6, 1.547 mg of B12 and 520 IU of A. The chicken eggs also included amino acids in the approximate quantities: 0.820 g of Lysine, 0.392 g of Methionine, 0.289 g of Cystine, 0.596 g of Threonine, 0.759 g of Isoleucine and 0.686 g of Phenylalanine.

Methionine and Cystine both include sulfur. Methionine is represented by the following structural formula.

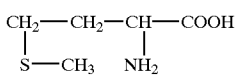

Cystine is represented by the following structural formula.

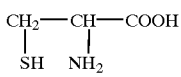

Since the eggshells and albumen contain amino acids that comprise sulfur, sulfur dioxide is created during the fermentation process. Sulfur dioxide is a colorless gas with a distinctive odor. The sulfur dioxide contributes to repelling the pests as it is placed on the leaf surfaces of the plant. The plants also absorb the sulfur present in the mixture of eggshells and albumen and give off a sulfur smell that repels pests.

Another important element in the pest repellent is sulfide. Sulfide is a chemical compound that contains sulfur and another element. All sulfides contain the sulfide ion, a single sulfur atom with an electrical charge of −2. Sulfide ions are present in some proteins which make up living things. Since eggs are high in proteins, sulfide is present in them. During the manufacturing process of the pest repellent sulfur from the sulfide is liberated by the fermentation process.

The best contemplated process for producing the pest repellant, involves collecting eggshells with part of the albumen attached thereto. The eggshells are placed into a metal or plastic container with warm or hot water. Over a period of time, the water coupled with bacteria and other fermenting agents dissolve the eggshells and cause them to decompose and liquefy. The mixture of water, eggshells and albumen are allowed to ferment for a period of time. Typically, the mixture ferments for at least twelve days. Heat may be introduced into the curing time to increase the fermentation process and cause chemical bonds to be broken thereby more quickly liberating sulfur. Likewise, the mixture may be stirred occasionally to increase the fermentation process. Typically, the mixture is tested using a hydrogen sulfide test kit to determine whether it is ready to be applied to plants. The mixture is ready for use as a pest repellant when the hydrogen sulfide is present in at least an amount of 0.424 mg/l.

The mixture is then strained to remove visible or non-liquid particles. Silt sized particles may remain in the mixture due to the calcium in the shells. Typically, the calcium carbonate of the egg shells does not breakdown entirely leaving silt sized particles which may be filtered from the mixture. In the preferred embodiment, the silt sized particles are left in the mixture and are applied at the base of the plant adding nutritional value to the mixture. The preferable ratios of chemical compounds in the mixture are 250 ml of $H_2O$ to 24.3 g of $CaCO_3$ to $1.06 \times 10^{-5}$ g of $H_2S$. The following is the structural formula for the pest repellant.

The following are examples of the effectiveness of the pest repellant mixture.

EXAMPLE 1

A mixture of hydrogen sulfide and calcium suspended in water, as mentioned above, was applied to a poinsettia plant. The poinsettia plant was placed near a gardenia bush that was infested with white flies. The poinsettia plant was monitored and visually inspected bi-weekly for approximately five months during warm weather. Visual inspections of the poinsettia plant revealed no white flies, larvae or white fly eggs present on the leaves of the poinsettia plant. The plant remained healthy and productive with blossoms and leaves of deep color.

EXAMPLE 2

A gardenia bush that was infested with white flies operated as a control. White flies were visibly present on the leave surface of the gardenia bush. A second gardenia bush was placed within approximately a foot of the control. The second gardenia bush was treated twice a month with a mixture containing 0.424 mg/l of $H_2S$ as mentioned above. Visual inspections of the gardenia bushes were conducted over a four-month period of time. While the control remained infested with white flies, no white flies were present during the visual inspections on the second gardenia bush. Further, neither larvae nor white fly eggs were found on the underside surface of the leaf. The second gardenia bush remained healthy and did not become infested with the white flies.

It is to be understood that the invention is not limited to the exact construction illustrated and described above, but that various changes and modifications may be made without departing from the spirit and the scope of the invention as defined in the following claims.

I claim:

1. A pest deterrent composition comprising water, calcium carbonate and at least 0.424 mg/l of hydrogen sulfide.

2. The pest deterrent composition according to claim 1 wherein said water is in an amount of 250 ml.

3. The pest deterrent composition according to claim 1 wherein said calcium carbonate is in an amount of 24.3 g.

4. The pest deterrent composition according to claim 1 wherein said hydrogen sulfide is in an amount of $1.06 \times 10^{-5}$.

5. The pest deterrent composition according to claim 1 further comprising:

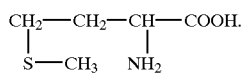

6. The pest deterrent composition according to claim 1 further comprising:

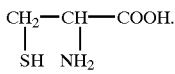

7. A method of controlling pests which comprises applying to a locus an effective amount of water, calcium carbonate and hydrogen sulfide composition given in the following formula:

250 ml $H_2O$;

24.3 g $CaCO_3$; and $1.06 \times 10^{-5}$ g $H_2S$.

8. A method for producing a pest deterrent composition comprising water, calcium carbonate and hydrogen sulfide, said method comprising the steps of:

placing egg shells with a portion of albumen attached thereto into a plastic or glass container;

pouring water having a temperature no greater than 21° C. over the egg shells; and allowing the mixture comprising the egg shells, a portion of albumen and water to ferment to produce a final mixture having at least at least 0.424 mg/l of hydrogen sulfide.

9. The method of claim 8 further comprising:

filtering silt material and particles from the final mixture.

10. The method of claim 8 further comprising:

applying or spraying said final mixture onto a gardenia plant.

11. The method of claim 8 further comprising:

applying or spraying said final mixture onto a poinsettia plant.

* * * * *